United States Patent [19]
Johnson

[11] B 3,988,590
[45] Oct. 26, 1976

[54] PHOTOMULTIPLIER TUBE GAIN REGULATING SYSTEM

[75] Inventor: Wayne F. Johnson, Loudon, Tenn.

[73] Assignee: The United States of America as represented by the United States Energy Research and Development Administration, Washington, D.C.

[22] Filed: Apr. 8, 1975

[21] Appl. No.: 566,572

[44] Published under the second Trial Voluntary Protest Program on March 16, 1976 as document No. B 566,572.

[52] U.S. Cl. ............................. 250/564; 250/207; 250/565; 356/197; 356/205
[51] Int. Cl.² ........................................ G01N 21/24
[58] Field of Search ............ 250/207, 214 AG, 564, 250/565, 573; 356/197, 205

[56] References Cited
UNITED STATES PATENTS

| | | | |
|---|---|---|---|
| 3,515,878 | 6/1970 | Ried, Jr. et al. | 250/207 |
| 3,555,284 | 1/1971 | Anderson | 250/565 |
| 3,783,300 | 1/1974 | Johnson | 250/564 |
| 3,800,161 | 3/1974 | Scott et al. | 250/564 |

OTHER PUBLICATIONS

*Automatic for Control For P.M. Tubes*, Brecke et al., IBM Technical Disclosure Bulletin, vol. 17, No. 7, Dec. 1974, pp. 2077-2078.

Primary Examiner—Archie R. Borchelt
Assistant Examiner—E. R. La Roche
Attorney, Agent, or Firm—Dean E. Carlson; D. S. Zachry; Louis M. Deckelmann

[57] ABSTRACT

This invention relates to an improved system for regulating the gain of a photomultiplier tube, and was designed for use with the photomultiplier tubes of a GeMSAEC fast analyzers. It has the following advantages over the prior system: noise is virtually eliminated; sample analysis can begin after 3 to 4 revolutions of the rotor; fluorescent and light scattering solutions can be used as a reference; and the reference solution can be in any cuvette on the rotor.

4 Claims, 1 Drawing Figure

U.S. Patent  Oct. 26, 1976  3,988,590
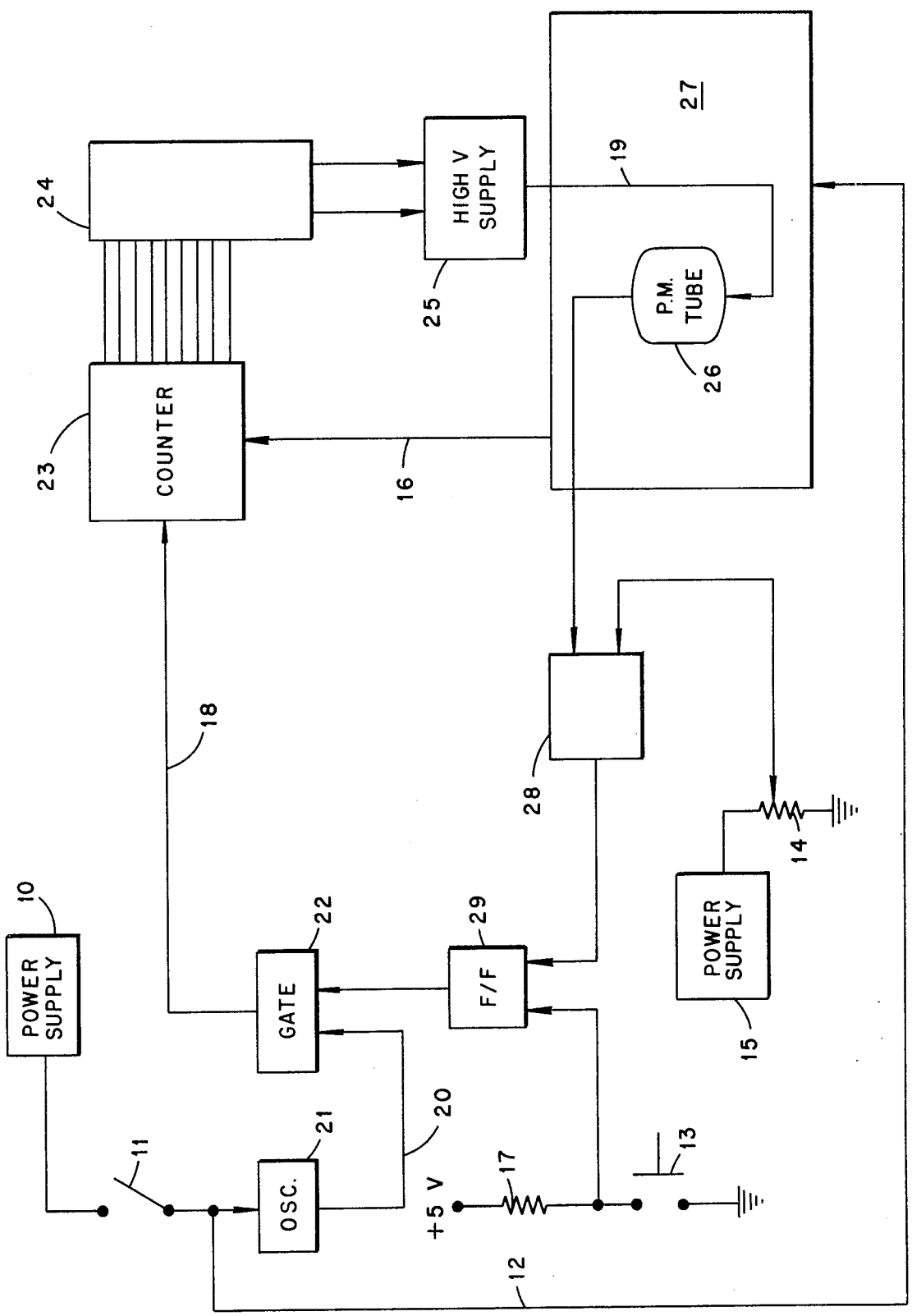

PHOTOMULTIPLIER TUBE GAIN REGULATING SYSTEM

This invention was made in the course of, or under, a contract with the Energy Research and Development Administration.

BACKGROUND OF THE INVENTION

The Molecular Anatomy (MAN) Program at the Holifield National Laboratory is involved in the development of clinical techniques for analyzing biomaterials on a molecular level. The GeMSAEC Fast Analyzer, a type of centrifuge, is one of the results of the program. The centrifuge is capable of analyzing the contents of minute samples placed in separate cuvettes on a rotor. The samples are spun around a light source and the analysis is made using one of four types of measurements, the amount of light the sample (1) absorbs, (2) fluorescences, (3) scatters, or (4) chemiluminescences. The measurements are made by a photomultiplier tube in the analyzer.

Two major problems exist with prior art circuits controlling the gain of the photomultiplier. One such prior circuit is described in U.S. Pat. No. 3,783,300, issued Jan. 1, 1974, to Wayne F. Johnson. One problem is the time required for the controller to set the gain on the P.M. tube. It is important to be able to begin the analysis as quickly as possible because reactions can begin to take place in the cuvettes in less than three tenths of a second. The prior method of setting the gain on the P.M. tube takes around 1.5 seconds. By that time, the reaction may have reached a steady state and valuable information is lost. The present invention, to be described hereinbelow, can begin analysis after 3 or 4 revolutions of the rotor. This is approximately 0.2 second at a rotor speed of 1000 rpm.

The other problem of prior art systems is that the reference cuvette has to be a water blank due to feedback complications. The prior P.M. tube controller can only use a water blank in the first cuvette as a reference. Other reference solutions tend to have a small degree of instability or noise during a run. A slight variation of the reference cuvette induces a large response in the feedback mechanism of the analyzer. For instance, assume the reference is a fluorescent solution that exhibited a small increase in fluorescence for a short time. The prior control system responds to this small increase by decreasing the results obtained in the cuvettes undergoing analysis. Thus, a small change in the reference solution greatly distorts the analysis results of the other cuvettes.

Thus, there exists a need for an improved system for regulating the gain of the photomultiplier tube of a photometric solution analyzer wherein the gain can be set at a desired or required level and in a shorter time interval, and the analyzer is not limited to a water blank cuvette as a reference. This need has been met in the present invention in a manner to be described hereinbelow.

SUMMARY OF THE INVENTION

It is the object of the present invention to provide an improved system for regulating or setting the gain of the photomultiplier tube of a photometric solution analyzer within a short time interval, and that is not limited to the use of a water blank cuvette as a reference.

The above object has been accomplished in the present invention by providing a control system wherein when the analyzer is turned on and an analysis is started, a comparator in the control system begins to compare the voltage level of the signal from the analyzer photomultiplier tube with an adjustable reference voltage. Immediately after the photomultiplier tube output voltage signal exceeds the reference voltage, the comparator signals a set-reset flip-flop to open a gate which is coupled between an oscillator and a high voltage supply circuit for the photomultiplier tube. Once the gate is opened, the high voltage supply circuit then maintains a constant gain in the photomultiplier tube for the entire run of the analyzer.

BRIEF DESCRIPTION OF THE DRAWING

The single FIGURE is a block diagram of the control system for regulating the photomultiplier tube gain in a GeMSAEC analyzer.

DESCRIPTION OF THE PREFERRED EMBODIMENT

The present invention was conceived for use with the fast photometric solution analyzer described in U.S. Pat. No. 3,555,284, issued Jan. 12, 1971, to Norman G. Anderson; with the miniature fast analyzer described in U.S. Pat. No. 3,798,459, issued Mar. 19, 1974, to Norman G. Anderson et al.; or with any other similar photometer system.

Referring now to the single FIGURE, the analyzer 27 may be one of the analyzers described in one of the above prior U.S. patents, for example. The high voltage for the photomultiplier tube 26 of the analyzer 27 is supplied by the power supply 25 which is controlled or regulated in a manner now to be described. A piezoelectric crystal oscillator 21 is activated by a power supply 10 when a switch 11 is closed. Also, when the switch 11 is closed, power for operating the other components of the analyzer 27 is supplied from the supply 10 through the switch 11 and the lead line 12.

A gate 22 is coupled to the output of the oscillator 21 by a lead line 20 and the gate 22 is coupled by a lead line 18 to a 10 bit binary counter unit 23. A set-reset flip-flop 29 is coupled to the gate 22 for controlling its open or closed state. The flip-flop 29 is set by means of a start switch 13 which, when closed, closes a circuit between a positively biased resistor 17 and ground. When the flip-flop 29 is thus set, it effects the closing of the gate 22 such that the impulses from the oscillator 21 pass through the gate 22 to the 10 bit binary counter 23. The counter counts and stores this information up to a maximum of 1024 impulses. The discrete impulses are converted to a direct current with a voltage range of zero to 10 volts by means of a digital-to-analog converter unit 24. The voltage output of the unit 24 is in direct proportion to the size of the input from the counter 23. So, if the input is 512 impulses, the voltage output will be 5 volts. If the input is 1024, the output will be 10 volts, etc.

Once the signal is converted to D.C. by the unit 24, it is relayed to the DC-DC high voltage supply 25 where it is amplified. As mentioned above, the high voltage supply is connected to the photomultiplier tube 26 in the GeMSAEC analyzer 27 by means of a lead line 19. The amplified signal determines the voltage gain in the photomultiplier tube 26. Next, the output voltage signal from the tube 26 is compared in a comparator 28 with a reference voltage from an adjustable voltage level source 14 which is connected between ground and a power supply 15. The reference voltage is set at a desired value depending on the type of measurement that the analyzer 27 is performing. The following is a list of the different types of possible light measurements performed by the analyzer and the voltage range for each measurement:

| Type of Measurement | Voltage Range |
| --- | --- |
| Absorption | 275–325 V D.C. |
| Light Scattering | 575–625 V D.C. |
| Fluorescent | 875–925 V D.C. |
| Chemiluminescent | 800–1000 V D.C. |

When the output voltage signal from the photomultiplier tube 26 is equal to or greater than the reference voltage, this means that the gain on the photomultiplier tube is high enough and should be maintained at that level, and at this time the comparator 28 signals the flip-flop 29 connected thereto. After the flip-flop 29 receives a signal from the comparator 28, it will then signal the gate 22 to open. Once the gate 22 is open, the binary counter 23 retains its count for the entire run of the analyzer 27 and thus maintains a constant gain on the photomultiplier tube 26 during this time. When analysis of all of the sample cuvettes has been completed, the 10 bit binary counter 23 receives an impulse oer a lead line 16 from the analyzer 27 which resets the output from the counter to zero. This prepares the system for the next run of the analyzer.

It should be understood that the present invention is not limited to the use of a water blank cuvette signal from the analyzer as a reference which is required in the above-mentioned prior art circuit in U.S. Pat. 3,783,300, due to feedback complications. The present invention does not require a feedback mechanism as does the above patented circuit such that fluorescent and light scattering solution can be used as a reference and the reference solution can be in any cuvette of the analyzer rotor whereby noise in the system of the present invention is virtually eliminated.

The control system described above can set the gain on the analyzer photomultiplier tube after 3 or 4 revolutions of the rotor which requires about 0.2 sec at a rotor speed of 1000 rpm, such that the analyzer can begin an analysis sequence at this time. By contrast, the above prior art patented circuit takes around 1.5 seconds to set the gain and, by that time, the reactions in the cuvettes may have reached a steady state and valuable information is lost.

This invention has been described by way of illustration rather than limitation andd it should be apparent that it is equally applicable in fields other than those described.

What is claimed is:

1. In an analytical photometer device including a multicuvette rotor provided with a plurality of cuvettes for receiving respective samples and reagents thereinto for mixing and reacting, means for rotating said rotor at a desired selected high speed, a stationary photometer system for scanning all of said cuvettes during rotation of said rotor, and a read-out device connected to the output of said photometer system for evaluating the signal received from each of said cuvettes during operation of said system, said photometer system including a photomultiplier tube, the improvement comprising control circuitry for setting the gain on said photomultiplier tube comprising an oscillator, a 10 bit binary counter, a gate connected between said oscillator and said counter, a digital-to-analog converter coupled to the output of said counter, a DC-DC high voltage supply coupled to the output of said converter, said converter providing a DC output to said high voltage supply in direct proportion to the size of the input from said counter, the output of said high voltage supply coupled to the input of said photomultiplier tube, a comparator, an adjustable reference voltage coupled as one input to said comparator, the output of said photomultiplier tube coupled as a second input to said comparator, a set-reset flip-flop, the output of said comparator coupled as one input to said flip-flop, a start switch, a positively biased resistor coupled as a second input to said flip-flop, said start switch when closed connecting said resistor to ground, the output of said flip-flop coupled to said gate such that when said start switch is closed said flip-flop effects the closing of said gate to permit impulses from said oscillator to pass to said binary counter, whereby when the output voltage from said photomultiplier tube is equal to or greater than said reference voltage as sensed by said comparator then said comparator provides a signal to said flip-flop for effecting an opening of said gate such that the impulses stored in said counter will then provide a constant gain to said photomultipler tube for a complete analytical run of said analyzer.

2. The device set forth in claim 1, wherein said reference voltage is set at a desired value depending which one of four possible types of measurements is to be made by said analyzer.

3. The device set forth in claim 2 wherein said four types of measurements are determined by the amount of light a sample absorbs, fluorescences, scatters, or chemiluminescences.

4. The device set forth in claim 1 wherein said constant gain is effected by said control circuitry about 0.2 second after said start switch is closed.

* * * * *